(12) United States Patent
Lawrence et al.

(10) Patent No.: US 9,212,551 B2
(45) Date of Patent: Dec. 15, 2015

(54) CHEMICAL SCAVENGER FOR DOWNHOLE CHEMICAL ANALYSIS

(75) Inventors: Jimmy Lawrence, Cambridge, MA (US); Huilin Tu, Watertown, MA (US); Jane Lam, Randolph, MA (US); Rekha Agarwalla, Quincy, MA (US); Ronald E. G. van Hal, Watertown, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 838 days.

(21) Appl. No.: 13/311,546

(22) Filed: Dec. 5, 2011

(65) Prior Publication Data

US 2012/0149604 A1  Jun. 14, 2012

Related U.S. Application Data

(60) Provisional application No. 61/422,637, filed on Dec. 13, 2010.

(51) Int. Cl.
| | |
|---|---|
| *C09K 8/12* | (2006.01) |
| *E21B 47/10* | (2012.01) |
| *E21B 49/10* | (2006.01) |
| *G01N 21/3577* | (2014.01) |
| *E21B 49/08* | (2006.01) |
| *G01N 11/00* | (2006.01) |

(52) U.S. Cl.
CPC ............ *E21B 49/10* (2013.01); *G01N 21/3577* (2013.01); *E21B 2049/085* (2013.01); *G01N 11/00* (2013.01)

(58) Field of Classification Search
CPC ............... C09K 8/24; C09K 8/32; C09K 8/36
USPC .......................................................... 507/119
See application file for complete search history.

(56) References Cited

U.S. PATENT DOCUMENTS

| | | | |
|---|---|---|---|
| 4,102,861 A | | 7/1978 | Wedel et al. |
| 4,339,349 A | | 7/1982 | Martin et al. |
| 4,994,671 A | * | 2/1991 | Safinya et al. ................ 250/255 |

(Continued)

FOREIGN PATENT DOCUMENTS

| | | |
|---|---|---|
| EP | 0193369 A2 | 9/1986 |
| WO | 2005001241 A2 | 1/2005 |

OTHER PUBLICATIONS

International Search Report and Written Opinion of PCT Application No. PCT/US2011/063674 dated Jul. 18, 2012.

(Continued)

*Primary Examiner* — John J Figueroa
(74) *Attorney, Agent, or Firm* — Daryl R. Wright; Jody DeStefanis

(57) ABSTRACT

A method for analyzing formation fluid in a subterranean formation is disclosed, wherein the method includes the steps of: adding a scavenger compound to an analytical reagent to form a reagent solution; collecting an amount of formation fluid into a formation tester, wherein the formation tester includes at least one fluids analyzer comprising at least one probe, at least one flow line, at least one reagent container, and at least one spectral analyzer, wherein the fluids analyzer is configured such that the collected formation fluid is fed through the at least one flow line to the at least one spectral analyzer; mixing an amount of the collected formation fluid with an amount of the reagent solution to form a mixture; and analyzing the mixture downhole.

17 Claims, 13 Drawing Sheets

(56) References Cited

U.S. PATENT DOCUMENTS

| | | |
|---|---|---|
| 5,762,141 A | 6/1998 | Hutchins et al. |
| 5,957,203 A | 9/1999 | Hutchins et al. |
| 5,965,615 A | 10/1999 | Kalvinsh et al. |
| 6,974,583 B2 | 12/2005 | Potin et al. |
| 7,595,074 B2 * | 9/2009 | Cholli et al. ............ 426/541 |
| 2004/0056186 A1 | 3/2004 | Simonetti et al. |
| 2005/0250666 A1 | 11/2005 | Gatlin et al. |
| 2005/0269499 A1 | 12/2005 | Jones et al. |
| 2007/0117215 A1 * | 5/2007 | Davis et al. ............ 436/172 |
| 2009/0192051 A1 | 7/2009 | Carman |
| 2009/0197781 A1 | 8/2009 | Sunkara |

OTHER PUBLICATIONS

Vogel, A. I., "Text-Book of Quantitative Inorganic Analysis, 3rd Edition," Chapter 10-12, John Wiley, 1961.

J. Lawrence, et al, "The degradation mechanism of sulfonated poly (arylene ether sulfone)s in an oxidative environment," Journal of Membrane Science, 2008, 325(2), pp. 633-640.

* cited by examiner

CHEMICAL SCAVENGER FOR DOWNHOLE CHEMICAL ANALYSIS

CROSS REFERENCE TO RELATED APPLICATIONS

This application claims the priority from U.S. Provisional Application No. 61/422,637 filed on Dec. 13, 2010. This application is incorporated by reference in its entirety.

BACKGROUND OF INVENTION

1. Field of the Invention

Embodiments disclosed herein relate generally to the analysis and characterization of downhole fluid components.

2. Background Art

Hydrocarbons are found in subterranean formations. Production of such hydrocarbons is generally accomplished through the use of rotary drilling technology, which requires the drilling, completing and working over of wells penetrating producing formations.

During drilling operations, it is desirable to perform various evaluations of the subterranean formations penetrated by the wellbore. In some instances, the drilling tool may be removed from the wellbore and a wireline tool may be deployed into the wellbore to test and/or sample the formation. In other cases, the drilling tool may be provided with devices to test and/or sample the surrounding formation and the drilling tool may be used to perform the testing and/or sampling. These samples or tests may be used, for example, to locate valuable hydrocarbons.

Formation evaluation often requires that fluid from the formation be drawn into the downhole tool for testing and/or sampling. Various devices, such as probes, may be extended from the downhole tool to establish fluid communication with the formation surrounding the wellbore and to draw fluid into the downhole tool. A typical probe is a circular element extended from the downhole tool and positioned against the sidewall of the wellbore. A rubber packer at the end of the probe may be used to create a seal with the wall of the wellbore. Another device used to form a seal with the wellbore is referred to as a dual packer. With a dual packer, two elastomeric rings expand radially about the tool to isolate a portion of the wellbore therebetween. The rings form a seal with the wellbore wall and permit fluid to be drawn into the isolated portion of the wellbore and into an inlet in the downhole tool.

Conventional methods for performing quantitative analysis of the collected downhole fluid require the sample to be brought to the surface and subsequently analyzed in a laboratory environment. However, recent advances in material science and miniaturization technology have enabled real-time measurements of the collected downhole fluid components using downhole sensors. Moreover, several studies using downhole optical, magnetic resonance, sonic, and electrochemical modules have demonstrated the feasibility to conduct various fluid characterizations downhole with comparable quality of measurements to those conducted in a controlled environment (e.g., in a laboratory).

Standard analytical procedures are available to do quantitative analysis of the collected downhole fluid by addition of a reagent that reacts chemically with a target species in the fluid sample to cause detectible changes in fluid property, such as color, absorption, spectra, turbidity, etc. See Vogel, A. I., "Text-Book of Quantitative Inorganic Analysis, $3^{rd}$ Edition," Chapter 10-12, John Wiley, 1961. Such changes in fluid property may be caused, for example, by the formation of a product that absorbs light at a certain wavelength, or by the formation of an insoluble product that causes turbidity, or bubbles out as gas. For example, addition of organic, pH sensitive dyes is used for colorimetric pH determination of downhole water samples. Specifically, the organic dyes are stored in a sample bottle, injected to the flow line, and mixed with the sample at pump out module prior to measurement.

However, due to the high pressure and temperature conditions downhole, the organic materials used in the reagents are prone to chemical attacks. For example, in the case where the reagent includes a polymer based compound, chemical attacks from oxidation and/or free radicals often change the structure and characteristics of the polymer, resulting in changes of color, viscosity, and structure stability of the reagent. Furthermore, thermal oxidation and free radical attack may cause chain scission of the polymer because its main chain and/or side chain scission rates are accelerated at high temperature. Additionally, these chemical attacks may result in degradation of the downhole reagent thereby decreasing the quality of the sampled fluid. Furthermore, such degradation of the downhole reagent may reduce or even prevent the desired changes in fluid properties from occurring and thereby diminish the accuracy of the analytical procedures conducted downhole (e.g., due to loss of coloration of the reagent).

Accordingly, there exists a need for downhole reagents having improved chemical and thermal stability against chemical attacks from free radical and/or other oxidative species at high temperatures. Similarly, there exists a need for improved downhole fluid measurement methods that exhibit improved chemical and thermal stability when subjected to downhole pressures and temperatures.

SUMMARY OF INVENTION

In one aspect, embodiments disclosed herein relate to a method for analyzing formation fluid in a subterranean formation is disclosed, wherein the method includes the steps of: adding a scavenger compound to an analytical reagent to form a reagent solution; collecting an amount of formation fluid into a formation tester, wherein the formation tester includes at least one fluids analyzer comprising at least one probe, at least one flow line, at least one reagent container, and at least one spectral analyzer, wherein the fluids analyzer is configured such that the collected formation fluid is fed through the at least one flow line to the at least one spectral analyzer; mixing an amount of the collected formation fluid with an amount of the reagent solution to form a mixture; and analyzing the mixture downhole.

In another aspect, embodiments disclosed herein relate to a composition for preventing and reducing the severity of chemical degradation caused by free radical attacks to chemical compounds and fluids used in downhole tools and oilfield operations, wherein the composition includes an analytical reagent and a scavenger compound.

Other aspects and advantages of the invention will be apparent from the following description and the appended claims.

DETAILED DESCRIPTION

The particulars shown herein are by way of example and for purposes of illustrative discussion of the embodiments of the present disclosed subject matter only and are presented in the cause of providing what is believed to be the most useful and readily understood description of the principles and conceptual aspects of the present disclosed subject matter. In this regard, no attempt is made to show structural details of the present disclosed subject matter in more detail than is necessary for the fundamental understanding of the present disclosed subject matter, the description taken with the drawings making apparent to those skilled in the art how the several forms of the present disclosed subject matter may be embodied in practice. Further, like reference numbers and designations in the various drawings indicated like elements.

In one aspect, embodiments disclosed herein relate to methods for analyzing and characterizing the fluid chemistry of a formation fluid in a subterranean formation. More specifically, embodiments disclosed herein relate to adding one or more chemical scavenger compounds to an analytical reagent to form a reagent solution having improved chemical and thermal stability, and reacting the reagent solution with downhole fluids so that the fluid chemistry of the downhole fluids may be analyzed and characterized.

Figure 1:
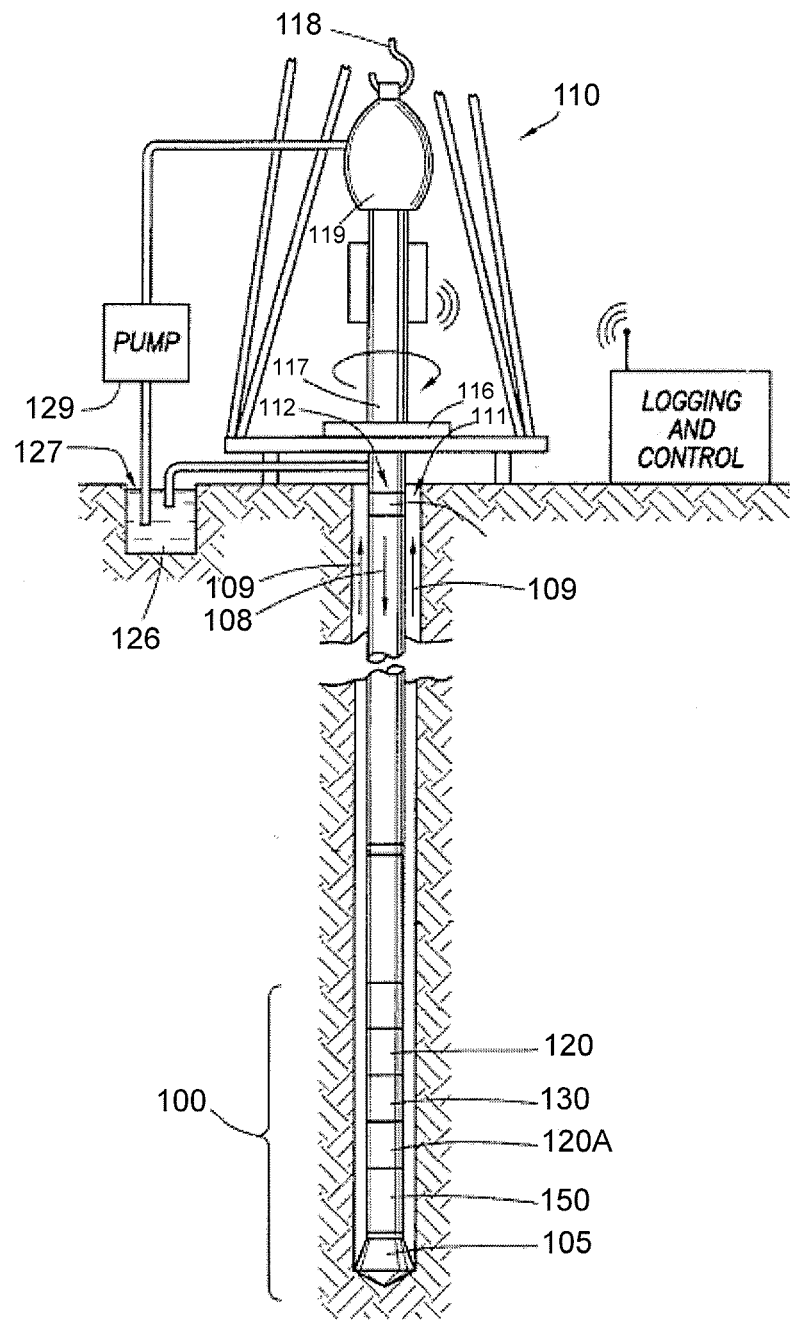
FIG. 1 shows a wellsite system in which one or more embodiments of the present disclosure may be used.

Referring to FIG. 1, a wellsite system in which one or more embodiments of the present disclosure may be employed is shown. The wellsite may be onshore or offshore. According to one or more embodiments of the present disclosure, a borehole 111 may be formed in a subsurface formation by rotary drilling using techniques well known in the art. One or more embodiments of the present disclosure may also use directional drilling.

As shown in FIG. 1, drill string 112 is suspended within the borehole 111 and has a bottomhole assembly (BHA) 100, which may include a drill bit 105 at its lower end. The surface system may include a platform and derrick assembly 110 positioned over the borehole 111, the assembly 110 including a rotary table 116, kelly 117, hook 118 and rotary swivel 119. The drill string 112 is rotated by the rotary table 116, energized by means not shown, which engages the kelly 117 at the upper end of the drill string. The drill string 112 is suspended from a hook 118, attached to a traveling block (also not shown), through the kelly 117 and a rotary swivel 119 which permits rotation of the drill string relative to the hook. As is well known, a top drive system could alternatively be used.

According to one or more embodiments of the present disclosure, the surface system may further include drilling fluid or mud 126 stored in a pit 127 formed at the wellsite. A pump 129 delivers the drilling fluid 126 to the interior of the drill string 112 via a port in the swivel 119, causing the drilling fluid to flow downwardly through the drill string 112 as indicated by directional arrow 108. The drilling fluid 126 exits the drill string 112 via ports in the drill bit 105, and then circulates upwardly through the annulus region between the outside of the drill string and the wall of the borehole, as indicated by directional arrows 109. In this well known manner, the drilling fluid lubricates the drill bit 105 and carries formation cuttings up to the surface as it is returned to the pit 127 for recirculation.

In one or more embodiment, the bottom hole assembly 100 further includes a logging-while-drilling (LWD) module 120, a measuring-while-drilling (MWD) module 130, a roto-steerable system and motor 150, and a drill bit 105.

According to one or more embodiment, the LWD module 120 is housed in a special type of collar, as is known in the art, and can contain one or more known types of logging tools. Although only one LWD module 120 and only one MWD module 130 is shown, it will also be understood that more than one LWD module and/or more than one MWD module can be employed, for example, as represented at 120A. (References, throughout, to a module at the position of 120 can alternatively mean a module at the position of 120A as well). The LWD module 120 includes capabilities for measuring, processing, and storing information, as well as for communicating with the surface equipment. In one or more embodiment, the LWD module may include a fluid sampling device.

According to one or more embodiment, the MWD module 130 is also housed in a special type of drill collar, as is known in the art, and can contain one or more devices for measuring characteristics of the drill string 112 and drill bit 105. The MWD tool further includes an apparatus (not shown) for generating electrical power to the downhole system. This may typically include a mud turbine generator powered by the flow of the drilling fluid; however, other power and/or battery systems may also be employed either in combination with or alternatively to a turbine. In one or more embodiment, the MWD module may include at least one of the following types of measuring devices: a weight-on-bit measuring device, a torque measuring device, a vibration measuring device, a shock measuring device, a stick slip measuring device, a direction measuring device, and an inclination measuring device.

Figure 2:
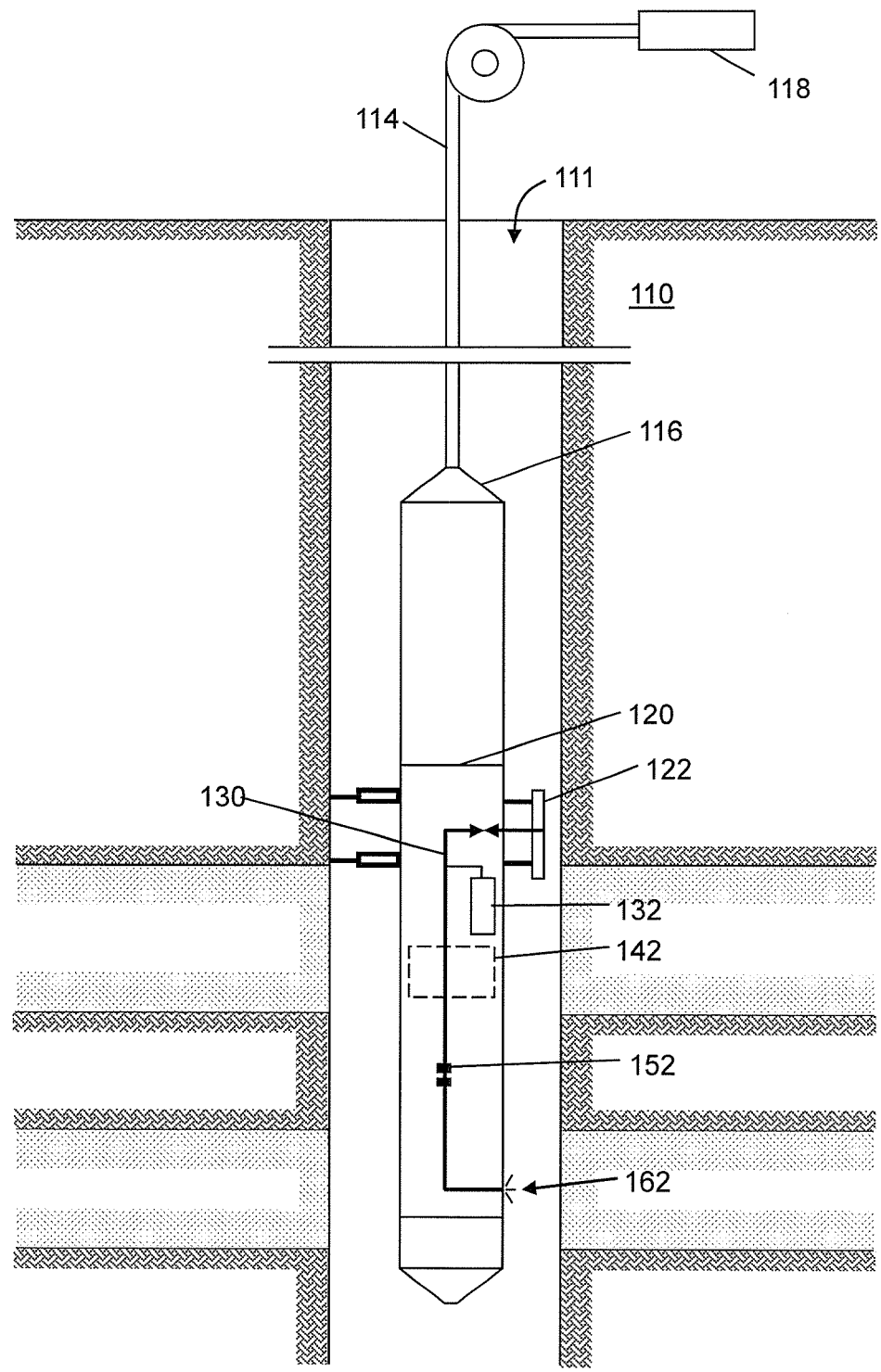
FIG. 2 shows a fluids analyzer in a wireline tool according to one or more embodiments of the present disclosure.

As shown in FIG. 2, in one or more embodiments of the present disclosure, rather than being disposed on a bottom hole assembly (as shown in FIG. 1) it may be possible to deploy an LWD module 120 downhole via a wireline tool.

Figure 3:
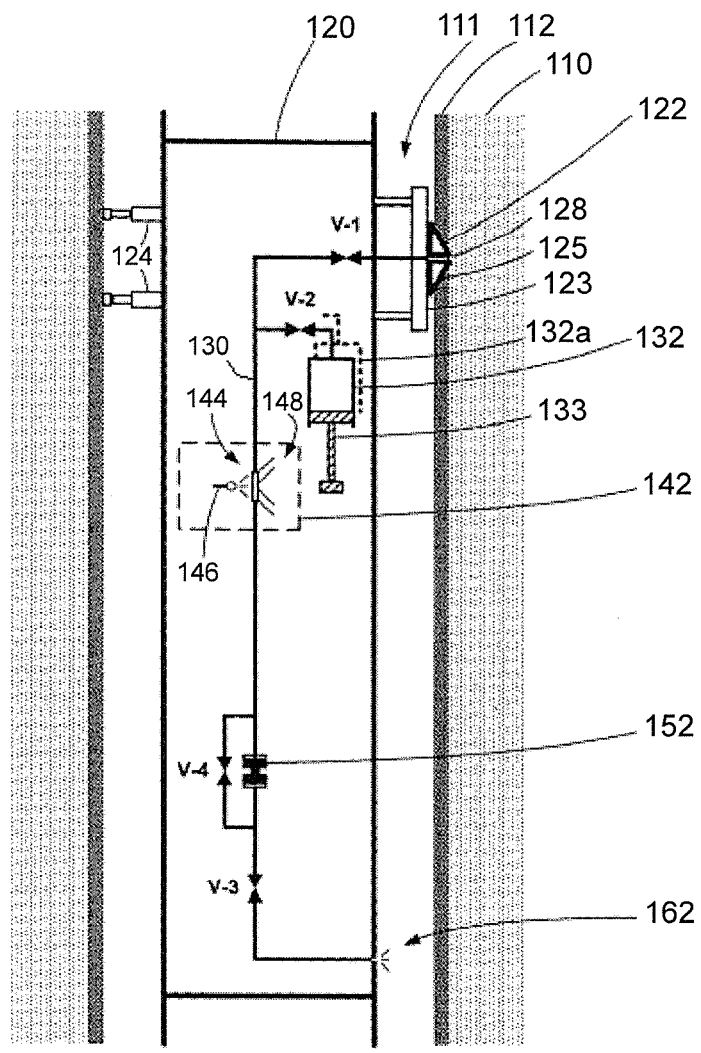
FIG. 3 shows detail of a fluids analyzer in a wireline tool according to one or more embodiments of the present disclosure.

Specifically, a wireline tool 116 may be deployed in a borehole 111 of a formation 110 to collect and analyze formation fluids. The wireline tool 116 may include fluids analyzer 120 (e.g., LWD module), which is capable of analyzing the collected formation fluids by measuring, for example, optical absorbance, pH, turbidity, fluorescence, turbidity viscosity, conductivity/resistivity, and magnetic resonance (NMR). A logging cable 114 suspends the wireline tool 116 within the borehole 111 and also couples the wireline tool 116 to a surface system 118. The major elements of the fluid analyzer 120 may include a probe 122, a fluid flow line 130, a reagent container 132 (having injector pump 133), an analyzer 142, a flow line pump (dual chamber piston pump) 152, and a main pump out line 162. Analyzer 142 may be selected from, for example, a spectral analyzer, a fluorescence detector, viscosity cell, resistivity cell or NMR tool. As shown in FIGS. 2 and 3, the probe 122, the fluid flow line 130, and the main pump out line 162 are shown in a single module; however, typical prior art formation testers include multiple modules sharing a single probe, a single flow line, and a single pump out line.

As shown in FIG. 3, the wireline tool 116 may be held in position, for example, by pistons 124, which may assist in applying force to push the tool 116 and/or probe 122 against the borehole 111 wall. Probe 122, which may be mounted to a carriage 123 and/or positioned in a stabilizer blade (not shown), can be extended to engage the borehole 111 wall such that fluid communication is established between the formation fluid and the fluid in the flow line 130 by penetrating the mud cake 112. A resilient packer 125 provides a seal while inflow aperture 128 is in fluid communication with the formation fluid. The resilient packer 125 seals the inflow aperture 128 and flow line 130 from wellbore pressure, which is usually greater than the formation pressure.

The flow line 130 may couple aperture 128 to analyzer 142 via a first flow line isolation valve V-1. It may also provide an entry point for fluid injection of reagent from the reagent container 132 via the reagent container isolation valve V-2. It may also couple analyzer 142 to the flow line pump 152, and, via second flow line isolation valve V-3, to the main pump-out line 162. Flow line 130 may have a cross-sectional area of approximately 0.2 cm$^2$ and may be a dual-chamber piston pump.

According to one or more embodiments of the present disclosure, analyzer 142 may be a conventional multi-channel (i.e., multi-wavelength) spectral analyzer, having a spectral analyzer cell 144, an illumination source 146, and an illumination detector 148. In such embodiments, the spectral analyzer 142 may have at least two channels, (e.g., because measuring pH may require a minimum of two channels). Optical density measurements may be made simultaneously on all channels at the rate of at least three per second, preferably higher. To accommodate measurements of a wide range of target measured properties, the spectral analyzer preferably has 3 or more channels, each channel measuring optical density at a different wavelength.

According to one or more embodiments of the present disclosure, fluids collected into the downhole wireline tool 116 using the probe 122 may be measured to determine, for example, pretest and/or pressure parameters. Additionally, once collected, the formation fluid may be injected with a predetermined volume of reagent solution to form a mixture of formation fluid and reagent solution in the flow line. Moreover, the formation fluid can be collected in a sample bottle that was partially filled with reagent solution, mixed and injected back in to the flowline for further analysis. Moreover, the formation fluid can be collected in a sample loop like in the Eyes II, mixed with a reagent solution and released to the flowline for further analysis. Moreover, small amounts of formation fluid might be pulled in to a microfluidic chip, mixed with a reagent solution and analyzed on chip. In at least one embodiment of the present disclosure, the reagent solution may include an analytical reagent and a scavenger compound. The analytical reagent and the scavenger compound may be selected based on the technique(s) used to analyze the collected sample. For example, the analytical reagent may be an organic material, such as an organic dye used to measure the pH of downhole water. In another example, the organic material may be a polymer based material used to detect downhole gas compounds. The reagent can also be simple organic molecules or polyelectrolytes dissolved in aqueous/non-aqueous solvents.

Additionally, in one or more embodiments of the present disclosure, the scavenger compound used to form the reagent solution may be selected based on the analytical reagent used. For example, where the analytical reagents are organic materials, the scavenger compound may be selected based on its ability to stabilize the organic materials at high temperatures. This is because the organic materials used to perform the analytical techniques mentioned above may be prone to degradation at downhole temperatures and pressures. Specifically, the organic materials may be prone to chemical attacks from, for example, free radicals and/or oxidation, at high temperatures. For example, where the organic material is a polymer based compound, these chemical attacks often change the polymeric structure and/or characteristics, which may result in changes in color, coloration, viscosity, and/or structure stability of the reagent. If the organic material is a dye, the structural change leads to a loose of coloration and/or changes in the response to the analyte. For example, pH sensitive dyes will not react or react differently to pH changes.

Additionally the scavenger compound used to from the reagent solution can stabilize the reaction product. This can be the case when organic compounds are formed but also when inorganic compounds like bismuth sulfide are formed.

According to one or more embodiments of the present disclosure, the scavenger compound may be a free radical scavenger having an adjustable free radical scavenging capacity based on the analytical reagent. As used herein, the term "free radical" is used to describe a molecule fragment with one or more unpaired electrons, for example, *Cl, *OH, *ClO, carbon compound radicals such as *CR$_1$(R$_2$)(R$_3$), and benzene like radicals. In an aqueous system, free radicals such as hydroxyl radicals may be formed through the formation of hydrogen peroxide (H$_2$O$_2$) and superoxide radical (*O$_2$) at high temperature, especially when free metal cations such as Fe$^{2+}$ exist. Free radicals may also be formed, for example, when a polymer decomposes at high temperature, thereby generating carbo-compound radicals. Several studies have indicated that free radicals are capable of attacking polymers and thereby causing their degradation by causing chain scission, especially at high temperatures. Specifically, free radical attack may cause chain scission of the polymer and its main chain and/or side chain because chain scission rates are accelerated at high temperatures. The process steps of polymer degradation from free radical oxidation can be explained as follows:

Initiation:

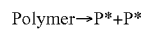

Propagation:

$$P^* + O_2 \rightarrow POO^*$$

$$POO^* + PH \rightarrow POOH + P^*$$

Chain Branching:

$$POOH \rightarrow PO^* + {}^*OH$$

$$PH + {}^*OH \rightarrow P^* + H_2O$$

$$PH + PO^* \rightarrow P^* + POH$$

$$PO^* \rightarrow \text{various chain scission reactions}$$

Termination:

$$POO^* + POO^* \rightarrow POOOOP \rightarrow POOP + O_2$$

$$P^* + POO^* \rightarrow POOP$$

$$P^* + P^* \rightarrow PP$$

As used herein, the term "free radical scavenger" is used to describe a compound that may be used to prevent the polymeric degradation described above by improving the chemical and/or thermal stability of an analytical reagent (e.g., organic material). For example, it is known that compounds with a hydroxyl functional group can donate one proton to an electrophilic radical and in turn form a double bond with the oxygen atom or create a resonance structure with the free radical compound. Free radical scavengers typically have polar functional groups or conjugated groups which are able to react with radicals to form more stable radical species with much lower reactivity. As a result, these compounds act as a sacrificial component, which results in a significant decrease in the degradation of the polymer.

In one or more embodiments of the present disclosure, a free radical scavenger compound may be used to prevent the chain scission described above by termination of the reactions shown above. Moreover, free radical scavenger compounds having chromophoric functional groups may also be used to indicate the presence and/or attack of free radicals in the system. The free radical scavenger works by trapping the reactive free radical compound. Free radical is reactive because its electronic structure is not stable. The scavenger has higher affinity to free radical and they form an intermediate structure. This intermediate structure can be in multiple configurations, resulting in energetically favorable states to maintain this intermediate structure. This compound then can be seen as a sacrificial compound, which was consumed by the free radical to form non-reactive species.

Free radical scavengers are known in the oil industry for polymer stabilization. For example, U.S. Pat. No. 5,957,203 discloses a gel that is used to block part of the formation and which can act as a fluid loss control agent in well completion and workover operations. The gels are formed from water-soluble polymers and a crosslinker, wherein the water-soluble polymers and the gels have the tendency to be unstable at higher temperatures. U.S. Pat. No. 5,957,203 suggests that the addition of a free radical scavenger may be used to stabilize the polymer and the gels. Similarly, U.S. Patent Application No. 2009/0192051 discloses that a free radical scavenger may be used to prevent the degradation of polymers used in a gel. It is suggested that the main reason to prevent degradation of the polymers is to prevent loss of functionality of the gel in time due to degradation.

In contrast to these examples, embodiments of the present disclosure are used to prevent degradation of the polymers so as to prevent the coloration of the polymer containing solution at downhole conditions. Specifically, according to one or more embodiments of the present disclosure, where colorimetric techniques are used to analyze the formation fluid, it is important that the reagent solution be able to maintain its color properties prior to being reacted with the formation fluid so that accurate analysis of the fluids may be performed. In such embodiments, the reagent solution may first be analyzed to establish a baseline, and thereafter reacted with the formation fluid in order to form a mixture that can be analyzed and compared to the established baseline.

According to one or more embodiments of the present disclosure, the reagent solution may include a small amount, for example, from about 0 to about 10%, of radical scavenger. In another embodiment, the reagent solution may include from about 10 to about 100 ppm of radical scavenger. In one or more embodiments, the solution may contain a solvent, wherein the solvent is selected from one of water, an organic solvent, an ionic liquid, or combinations thereof. The solution may or may not contain other components like metal ions, metal ions complexed with simple molecules or polyelectrolytes, metal containing polymers or a combination thereof.

A broad range of chemicals can be used as radical scavengers for the present disclosure, including, for example, alcohols, phenols, thiols, amines, phosphines, silanes, siloxanes, and alkyl halides. According to one or more embodiments of the present disclosure, the free radical scavenger may be one or more of the following: butyl hydroxy toluene (BHT); butyl hydroxyanisole (BHA); tertiary butyl hydroquinone (TBHQ); mono-tert butyl hydroquinone (MTBHQ); ascorbic acid; isopropyl alcohol (IPA); and propyl gallate.

It is important, however, that the free radical scavenger be selected according to the conditions of the system and environment. For example, ascorbic acid degrades at temperatures greater than about 100° C. and therefore may not be suitable for high temperature operations (e.g., temperatures greater than about 150° C.). However, as shown in Example 3, isopropyl alcohol works well at such temperatures despite having less radical scavenging capacity compared to ascorbic acid. Additionally, hindered amine compounds, although they are not specifically strong radical scavengers, may act as radical inhibitors/radical transfer agents, thereby inhibiting the reaction rate. Radical inhibitors may be used to create a slow polymerization.

According to one or more embodiment of the present disclosure, free radical scavengers suitable for use in the present disclosure may include alcohol based scavenging agents such as compounds having the following formula:

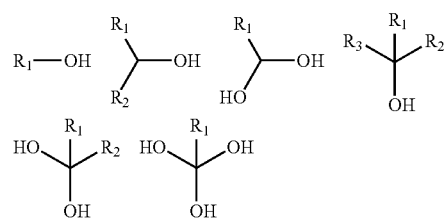

wherein $R_1$ may be alkyl (typically with 1-20 carbon atoms), alkenyl (typically with 1-20 carbon atoms), and alkynyl groups (typically with 1-20 carbon atoms) as well as halogen, ether, ester, ketone, aldehyde and amide-derived alkyl, alkenyl, and alkynyl groups, and $R_2$ and $R_3$ may be hydrogen, alkyl (typically with 1-20 carbon atoms), alkenyl (typically with 1-20 carbon atoms), and alkynyl groups (typically with 1-20 carbon atoms) as well as halogen, ether, ester, ketone, aldehyde and amide-derived alkyl, alkenyl, and alkynyl groups.

In another embodiment of the present disclosure, free radical scavengers suitable for use in the present disclosure may include radical scavenging agents with polyphenol functionality, such as compounds having the following formula:

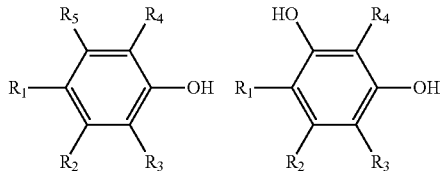

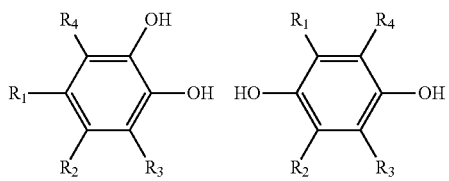

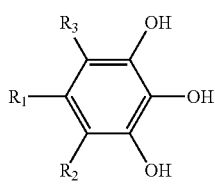

wherein $R_1$, $R_2$, $R_3$, $R_4$ and $R_5$ may be hydrogen, halogen, phenyl, benzyl, alkyl (typically with 1-20 carbon atoms), alkenyl (typically with 1-20 carbon atoms), and alkynyl groups (typically with 1-20 carbon atoms) as well as halogen, ether, ester, ketone, aldehyde and amide-derived alkyl, alkenyl and alkynyl groups. In addition, $R_1$, $R_2$, $R_3$, $R_4$ and $R_5$ may be hydroxyl, carbonyl, ester, amide groups etc.

In yet another embodiment of the present disclosure, free radical scavengers suitable for use in the present disclosure may include amine, hindered amine, and nitroxide based radical scavenging agents, such as compounds having the following formula:

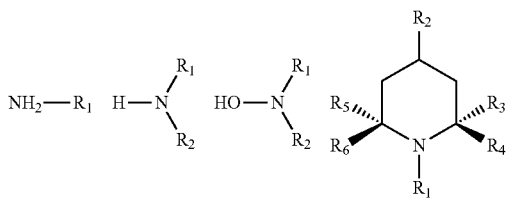

wherein $R_1$, $R_2$, $R_3$, $R_4$, $R_5$, and $R_6$ may be hydrogen, halogen, phenyl, benzyl, alkyl (typically with 1-20 carbon atoms), alkenyl (typically with 1-20 carbon atoms), and alkynyl groups (typically with 1-20 carbon atoms) as well as halogen, ether, ester, ketone, aldehyde, and amide-derived alkyl, alkenyl and alkynyl groups. In addition, $R_1$, $R_2$, $R_3$, $R_4$, $R_5$, and $R_6$ may be hydroxyl, carbonyl, ester, amide groups etc.

More specifically, according to one or more embodiment, an alcohol based radical inhibitor and antioxidant with polyphenol functionality may be used for terminating, inhibiting and/or retarding highly reactive free radicals and thus stabilizing the reagents of interests. This will be useful to change the ionic properties of the system, improve the solubility of specific reagent components, improve viscosity, providing specific optical absorption, etc. The polyphenols may be one of the following compounds:

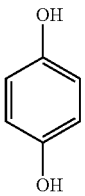

Hydroquinone (HQ)

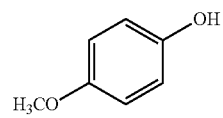

Hydroquinine monomethyl ether (MEHQ)

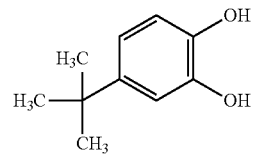

4-tert-butylcatechol (TBC)

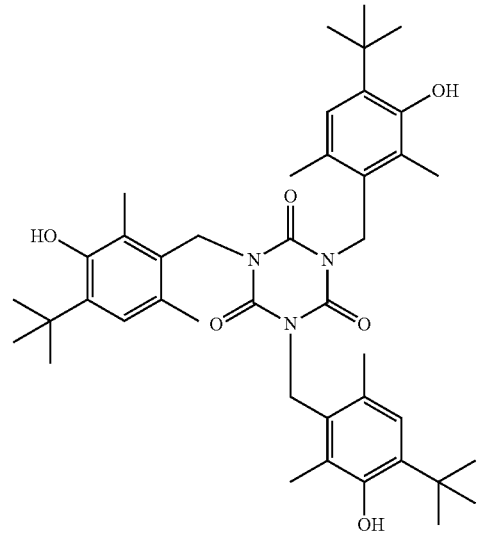

1,3,5-Tris(4-tert-butyl-3-hydroxy-2,6-dimethylbenzyl)-1,3,5-triazine-2,4,6-(1H, 3H, 5H)-trione (Irganox 1790)

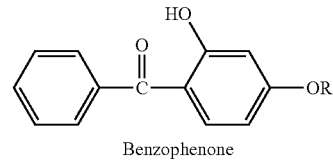

Benzophenone

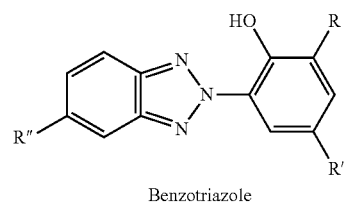

Benzotriazole

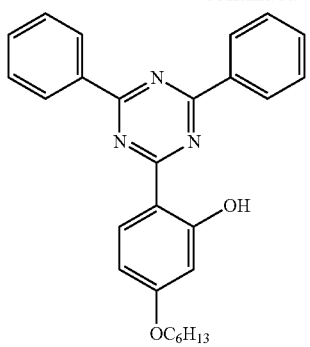

Hydroxyphenyl triazine

In another embodiment, an amine based radical inhibitor may be used and may have the following structure:

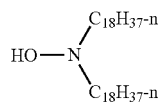

Diotadecylhydroxylamine

In yet another embodiment, a hindered amine and nitroxide based radical inhibitor may be used and may have one of the following structures:

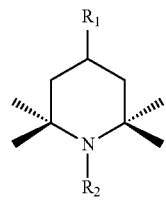

Hindered amine stabilizer (HAS) or
hindered amine light stabilizer (HALS)

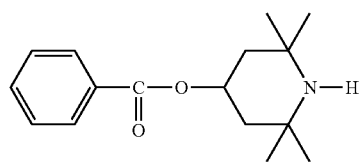

I

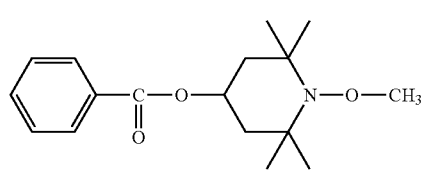

II

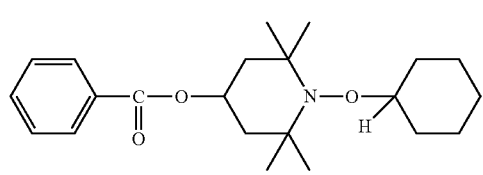

III

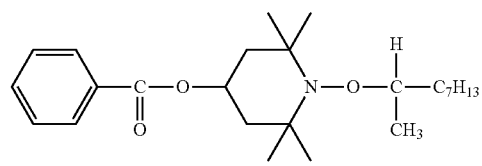

IV

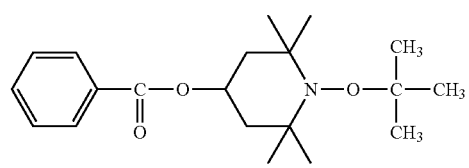

V

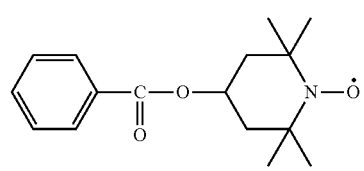

VI

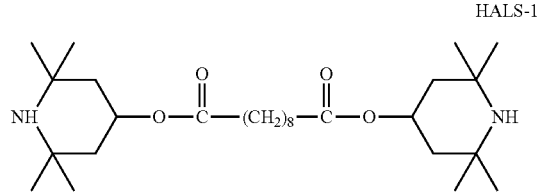

HALS-1

Tinuvin 770

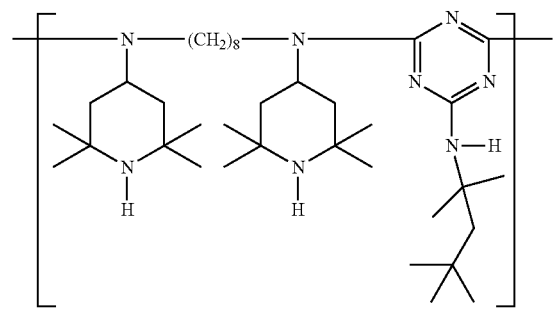

HALS-2

Chimassorb 944

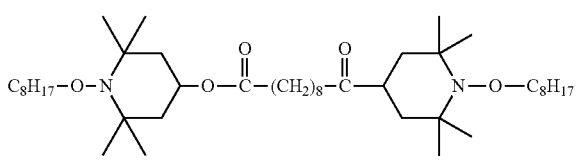

HALS-3

Tinuvin 123

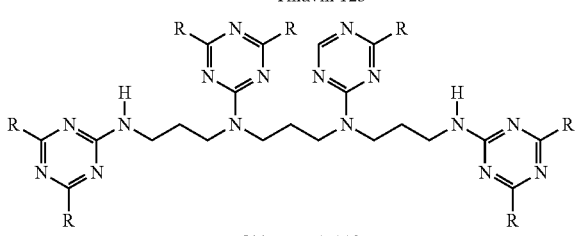

Chimassorb 119

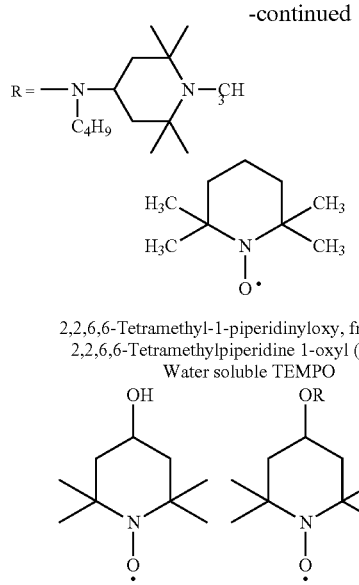

2,2,6,6-Tetramethyl-1-piperidinyloxy, free radical,
2,2,6,6-Tetramethylpiperidine 1-oxyl (TEMPO)
Water soluble TEMPO R = hydroxyl terminated alkyl groups

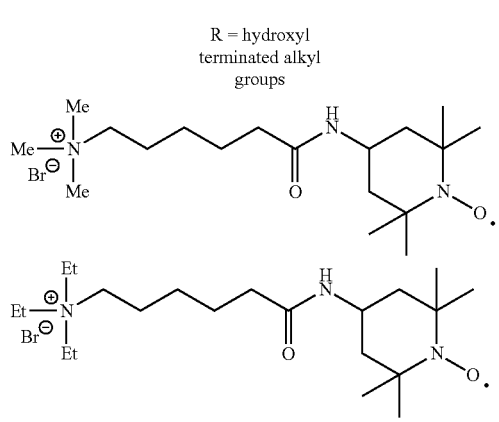

Figure 4:
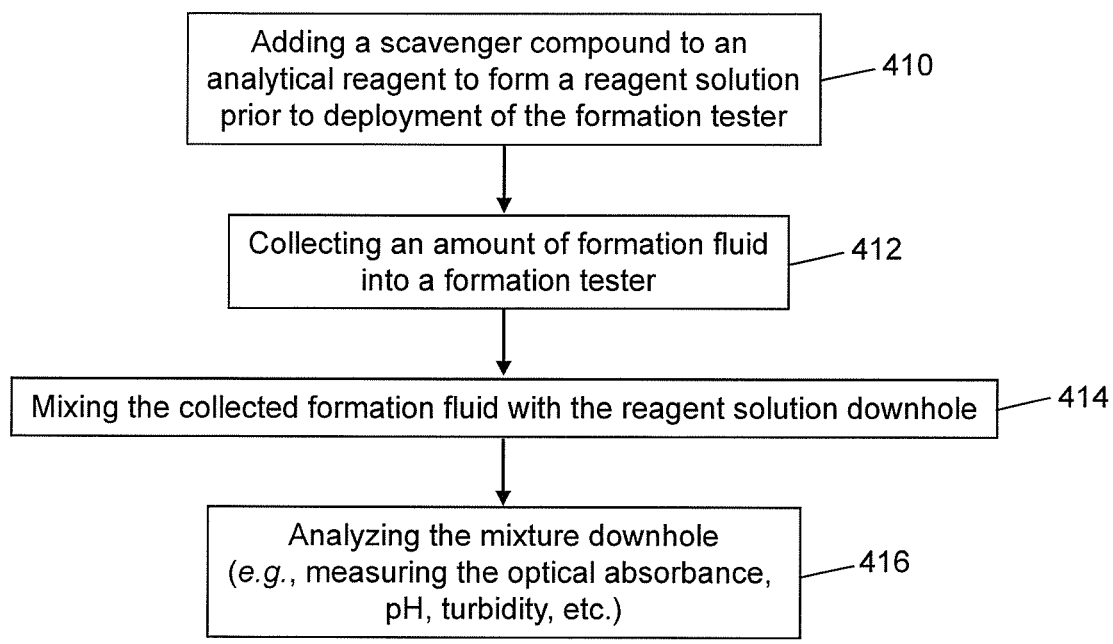
FIG. 4 shows a flowchart illustrating one or more embodiments of a method of the present disclosure.

As shown in FIG. 4, according to one or more embodiments of the present disclosure, a method for analyzing formation fluid in a subterranean formation may include adding a scavenger compound to an analytical reagent to form a reagent solution 410. Specifically, adding a scavenger compound may involve adding a small amount, for example, 10-100 ppm of the scavenger compound to stabilize the reagent solution. Additionally, as shown in FIG. 4, a method according to one or more embodiments of the present disclosure may further include the steps of collecting an amount of formation fluid into a formation tester 412, mixing an amount of the collected formation fluid with the reagent solution to form a mixture downhole 414, and analyzing the mixture downhole 416.

According to one or more embodiments of the present disclosure, the step of analyzing the mixture downhole 416 may include, for example, performing spectral analysis on the mixture. Specifically, in one embodiment, performing spectral analysis may include reagent solution injection, wherein the performing reagent solution injection spectral analysis includes injecting the reagent solution into the formation fluid within the flow line to create a mixture of formation fluid and reagent solution in the flow line. Other analytical techniques may include, for example, fluorescence, turbidity, viscosity, conductivity/resistivity and magnetic resonance (NMR) measurements.

Additionally, according to one or more embodiments of the present disclosure, the method for analyzing the formation fluid may further include the step of establishing and storing baseline optical density values for at least one wavelength prior to injection of the reagent solution. Specifically, in one embodiment, this may include analyzing (e.g., using spectral analysis) the collected formation fluid in its purest form, i.e., after collection but prior to injection of the reagent solution. This may provide analytical data that may be subsequently used for comparison of formation fluids and/or characterization of formation fluids.

Figure 5:
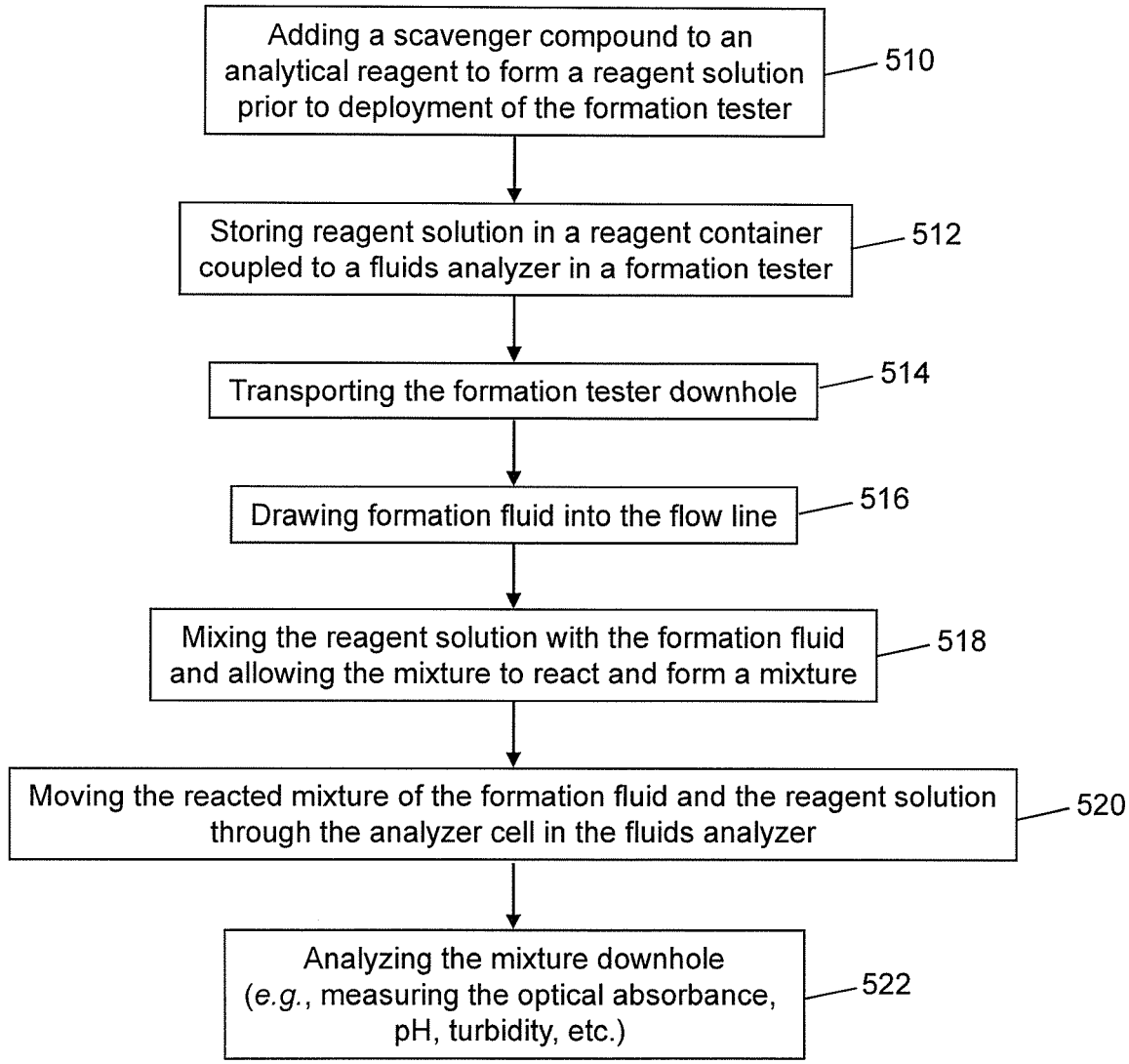
FIG. 5 shows a flowchart illustrating one or more embodiments of a method of the present disclosure.

As shown in FIG. 5, according to one or more embodiments of the present disclosure, a method for analyzing the fluid chemistry of a formation fluid in a subterranean formation may include adding a scavenger compound to an analytical reagent to form a reagent solution 510, storing the reagent solution in a reagent container coupled to a fluids analyzer via a flow line in a formation tester 512, transporting the formation tester downhole 514, drawing a predetermined amount of formation fluid into the flow line 516, mixing the reagent solution with the formation fluid and allowing the mixture to react and form a mixture 518, moving the reacted mixture of the formation fluid and the reagent solution through the analyzer cell in the fluids analyzer 520, and analyzing the mixture downhole 522. In other embodiments of the present disclosure, a method for analyzing the fluid chemistry of a formation fluid in a subterranean formation may include using a sample bottle, flow loop, and/or microfluidics. In yet other embodiments, the sampling may include combining a volume of downhole fluid with a volume of reagent in a sample chamber, and subsequently mixing the mixture in a bottle, and finally injecting the mixture out to optic and/or other modules, thereby enabling accurate quantitative analysis.

According to one or more embodiments of the present disclosure, the scavenger compound and the analytical reagent may be combined in the reagent container prior to deployment of the tool downhole. Once the tool has been deployed downhole and the formation fluids have been collected, the collected fluids and the reagent solution may be combined and reacted to form a mixture. This mixture may then be analyzed either at the surface or downhole in the analyzer cell.

EXAMPLES

Figure 6A:
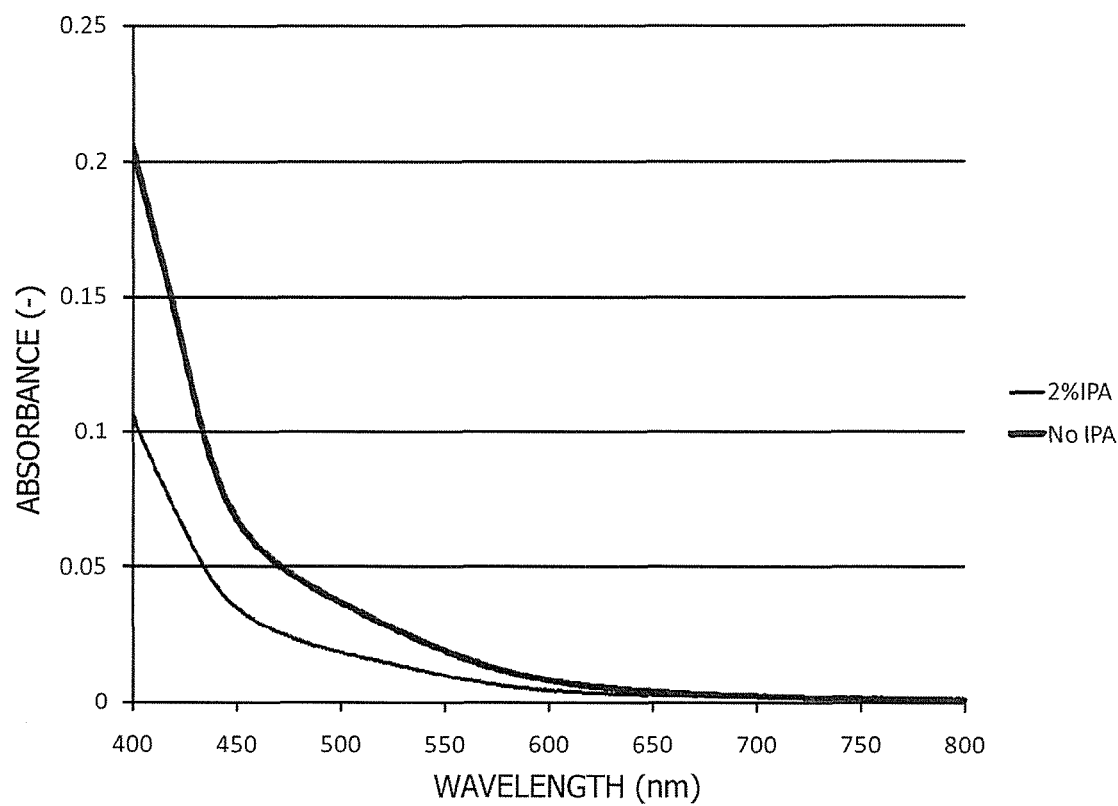
FIG. 6A shows the optical absorbance spectrum of a poly (4-styrenesulfonic acid) with and without IPA according to one or more embodiments of the present disclosure after 20 hours at 150 deg C.
Figure 6B:
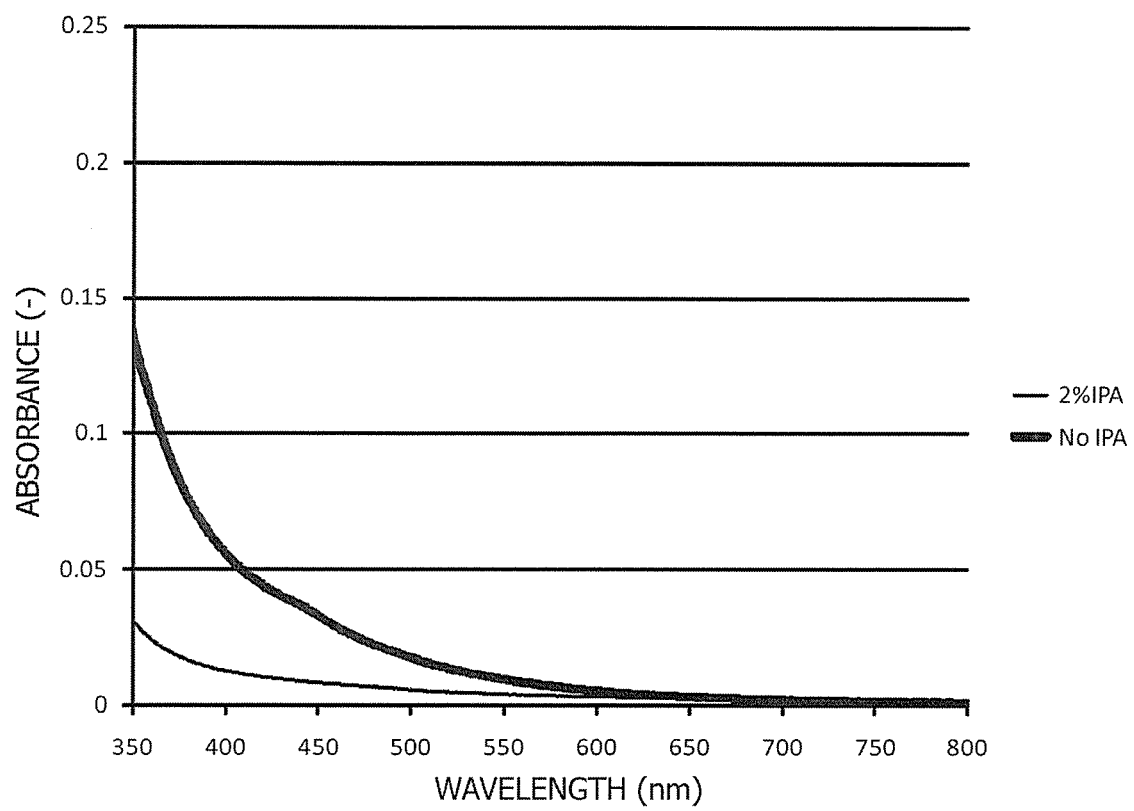
FIG. 6B shows the optical absorbance spectrum of a poly (vinylpyrolidone) with and without IPA according to one or more embodiments of the present disclosure after 20 hours at 150 deg C.

FIGS. 6A-B show the influence of 2% isopropyl alcohol scavenger on the aging process of several soluble polymers. These polymers are both suitable candidates to be used in chemical detection of specific components in formation fluids by absorption spectroscopy. FIG. 6A shows the UV-Vis spectra of 1.75 weight % poly(4-styrenesulfonic acid) with and without isopropyl alcohol after 20 hours at 150 deg C. FIG. 6B shows the UV-Vis spectra of 1.75 weight % poly(vinylpyrolidone) with and without isopropyl alcohol after 20 hours at 150 deg C.

Figure 7A:
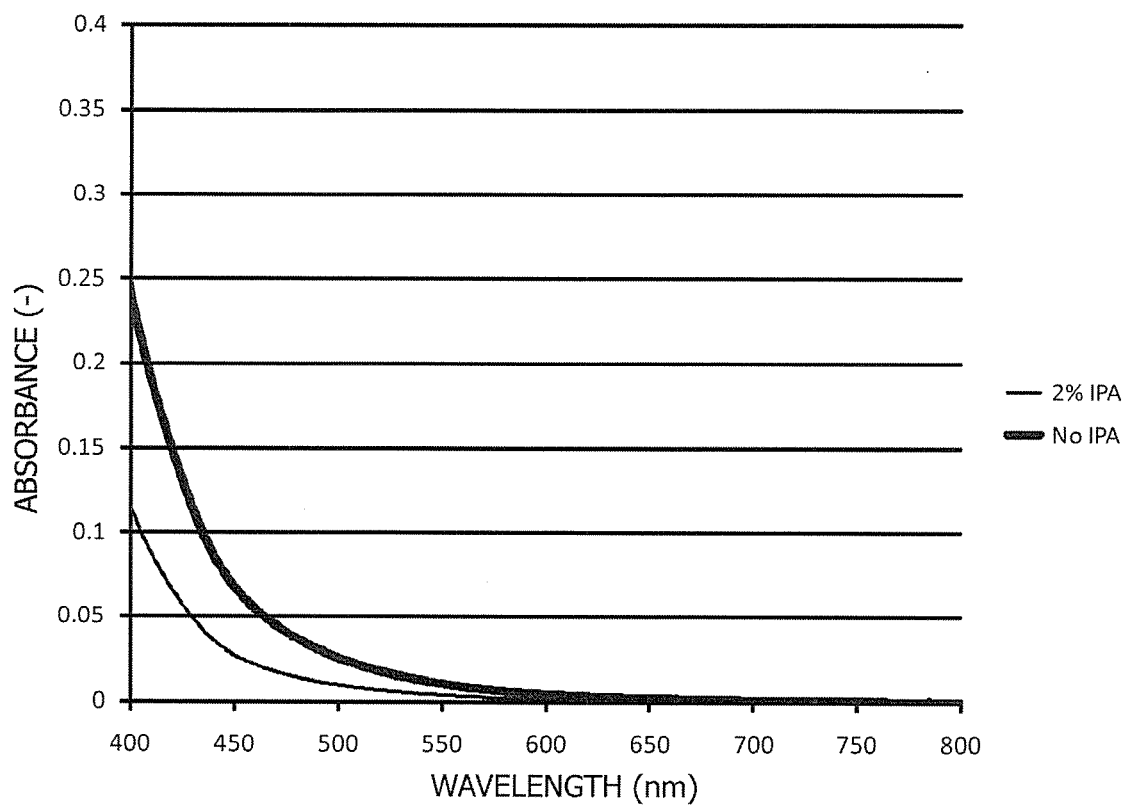
FIG. 7A shows the optical absorbance spectrum of a poly (4-styrenesulfonic acid) and 0.06% hydrogen peroxide with and without IPA according to one or more embodiments of the present disclosure after 20 hours at 120 deg C.
Figure 7B:
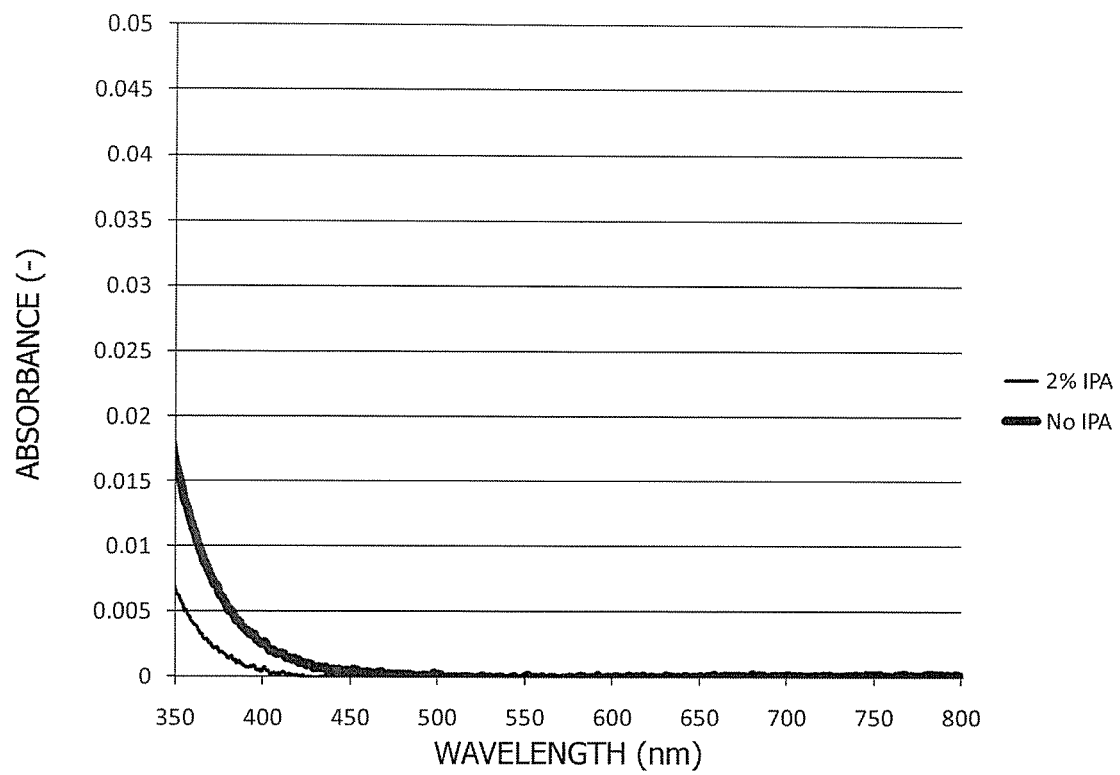
FIG. 7B shows the optical absorbance spectrum of a poly (acrylic acid) and 0.06% hydrogen peroxide with and without IPA according to one or more embodiments of the present disclosure after 20 hours at 120 deg C.
Figure 7C:
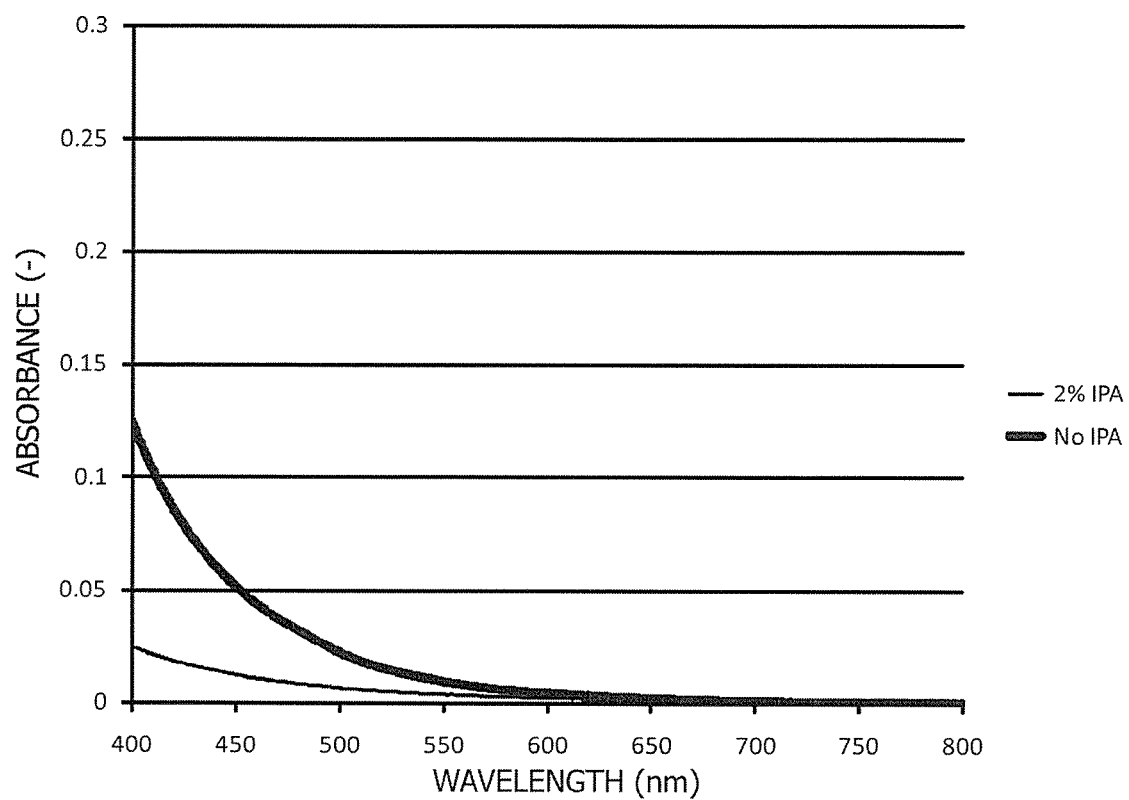
FIG. 7C shows the optical absorbance spectrum of a poly (acrylamide-co-acrylic acid) and 0.06% hydrogen peroxide with and without IPA according to one or more embodiments of the present disclosure after 20 hours at 120 deg C.

FIGS. 7A to 7C show the influence of isopropyl alcohol scavenger on the aging process of several soluble polymers. These polymers are both suitable candidates to be used in chemical detection of specific components in formation fluids by absorption spectroscopy. In this experiment 0.06% hydrogen peroxide was added to the solution to generate radicals. Hydrogen peroxide is commonly used to generate radicals at higher temperatures. FIG. 7A shows the UV-Vis spectra of poly(4-styrenesulfonic acid) with and without isopropyl alcohol after 20 hours at 120 deg C. In the absence of hydrogen peroxide these solutions didn't show any coloration after heating for 20 hours at 120 deg C. FIG. 7B shows the UV-Vis spectra of poly(acrylic acid) with and without isopropyl alcohol after 20 hours at 120 deg C. In the absence of hydrogen peroxide these solutions did not show any coloration after heating for 20 hours at 120 deg C. FIG. 7C shows the UV-Vis spectra of poly(acrylamide-co-acrylic acid) with and without isopropyl alcohol after 20 hours at 120 deg C. In the absence of hydrogen peroxide these solutions didn't show any coloration after heating for 20 hours at 120 deg C.

Figure 8A:
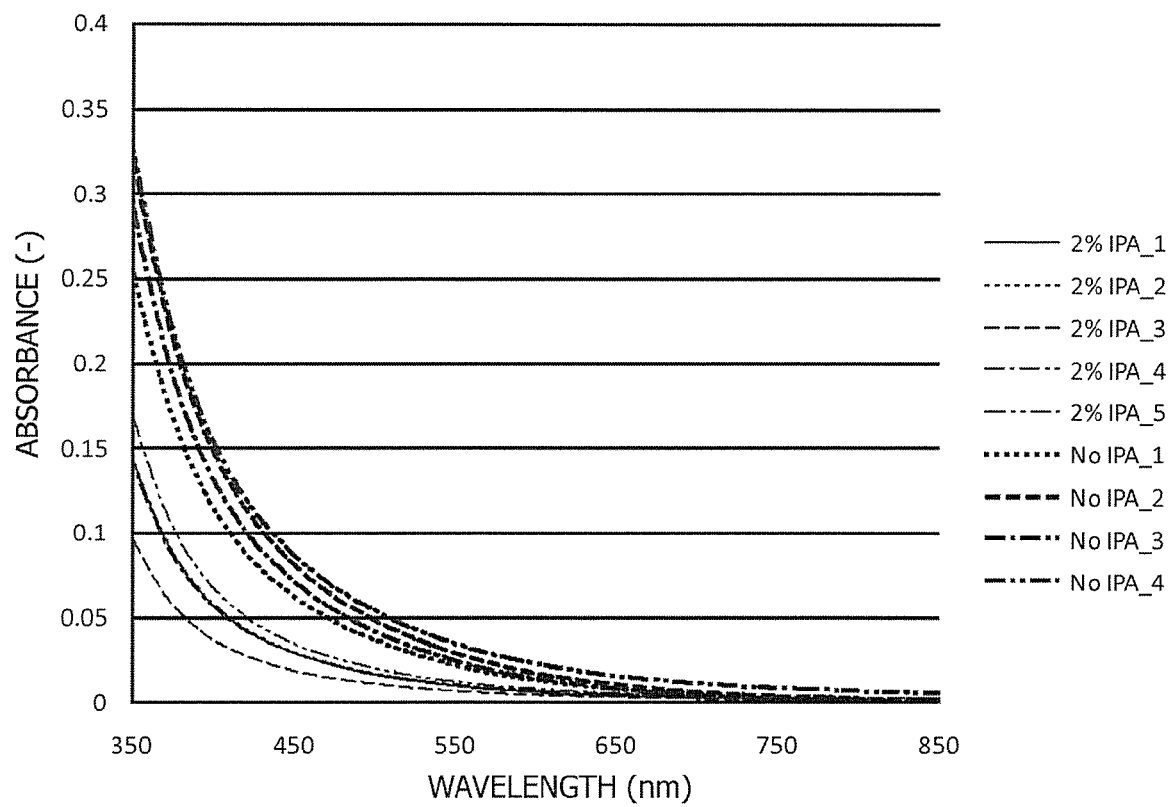
FIG. 8A shows the optical absorbance spectrum of 5 poly (acrylic acid) solutions with IPA and 4 poly(acrylic acid) without IPA according to one or more embodiments of the present disclosure.
Figure 8B:
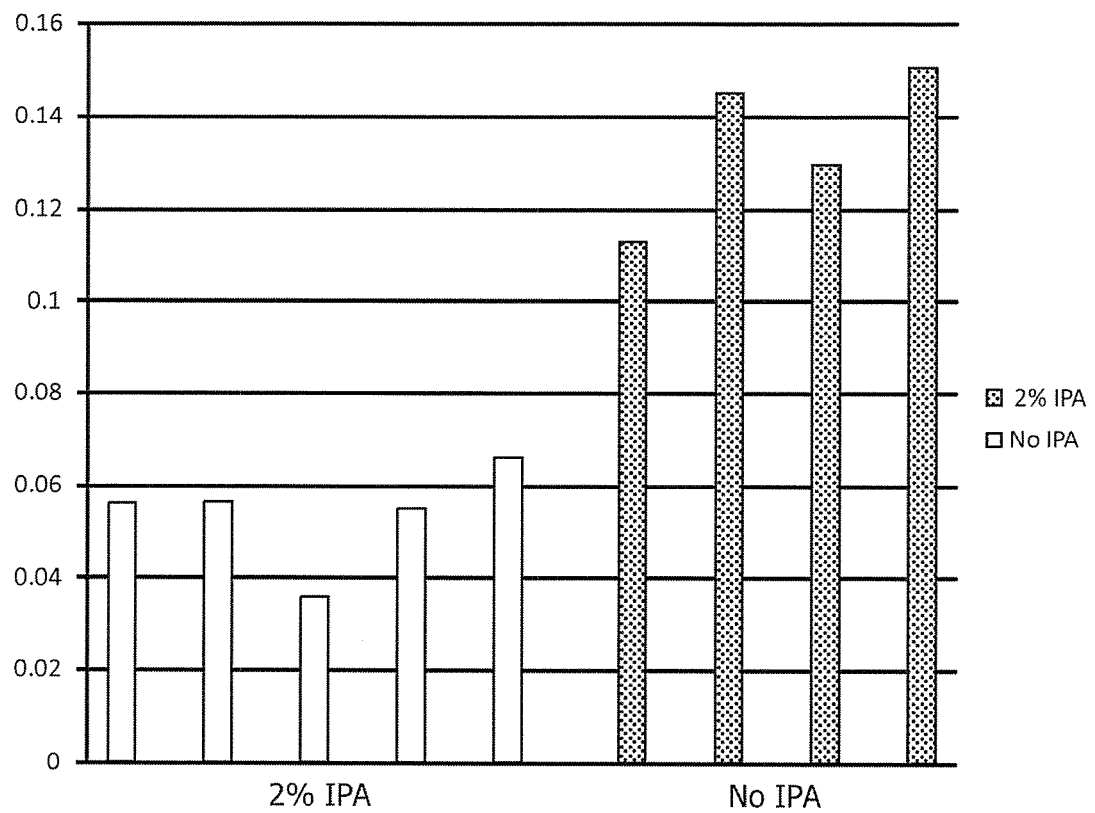
FIG. 8B shows the optical absorbance at 400 nm of the one or more embodiments shown in FIG. 8A.

Two sets of polymer-based reagents were prepared, one without addition of a free radical scavenger, the other having isopropyl alcohol added thereto. As shown in FIGS. 8A and 8B, the optical absorbance of the solutions was compared after the solutions were heated at 150° C. for 24 hours. FIG. 8A shows the UV-Vis absorption of polyacrylic acid aqueous solution, both with and without addition of isopropyl alcohol. Prior to heating treatment, the UV-Vis spectra of these solutions did not have optical absorption (i.e., Abs=0, flat spectra) from 400 to 1000 nm. As shown in FIGS. 8A and 8B, the addition of the radical scavenger compound, i.e., isopropyl alcohol, increased the structural stability of the polymer-based solution at high temperatures. FIG. 8B shows optical absorbance at 400 nm, 400 nm corrected at 800 nm as baseline of solutions without isopropyl alcohol and with isopropyl alcohol addition after heating at 150° C. for 24 hours. These examples show that the addition of IPA reduces the coloration of the solution at high temperature which is of importance since these solutions are used for colorimetric detection of compounds in formation fluids. For example, the optical spectrum of the polymer based reagent solution is taken after reaction with a compound in the formation fluid to determine the concentration of this formation fluid. Furthermore, these results prove that the polymer solution has changed and thus the characteristics in conductivity, viscosity, fluorescence, etc. will have changed as well.

Figure 9:
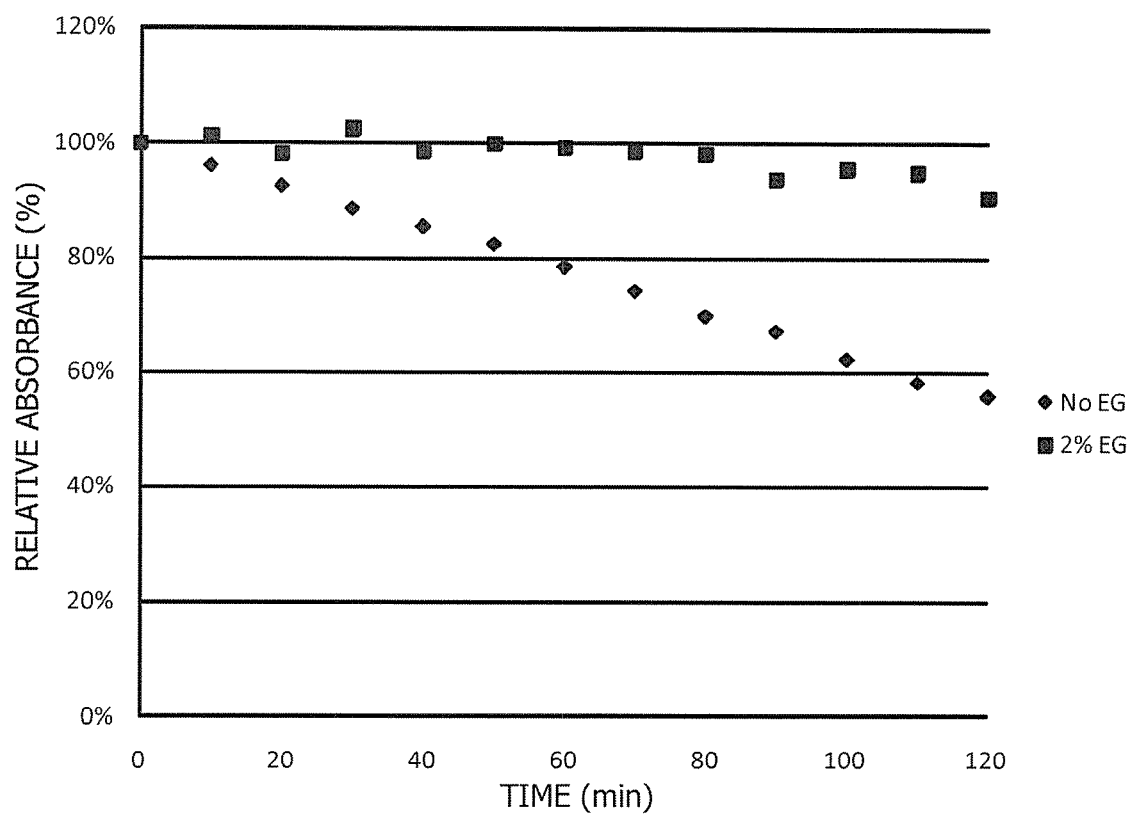
FIG. 9 shows the decrease in optical absorbance of dissolved bismuth sulfide with and without ethylene glycol at 150 deg C.

As shown in FIG. 9, a reagent mixture containing bismuth ions with and without ethylene glycol is reacted with hydrogen sulfide at 150 deg C. The reagent mixture can be used to detect hydrogen sulfide in gas or water where the optical absorbance is linear dependent of the sulfide concentration in the sample. FIG. 9 shows the optical absorbance at 400 nm at 150 deg C over time. It can be seen that the optical absorbance without ethylene glycol decreases much faster than with ethylene glycol.

Advantageously, embodiments of the present disclosure may provide improved methods for collecting and analyzing formation fluids downhole. Specifically, embodiments of the present disclosure may provide a free radical scavenger having an adjustable free radical scavenging capacity that may be used to prevent or reduce the severity of chemical degradation caused by free radical attacks on chemical compounds and fluids used in downhole tools and oilfield operations. Additionally, embodiments of the present disclosure may enhance the thermal stability of a downhole reagent by preventing degradation to the downhole reagent and prevent the quality decrease of sampled fluid. Embodiments of the present disclosure may make it possible to run the downhole chemical system at harsher conditions, such as higher temperature range or longer operation time.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed:

1. A method for analyzing formation fluid in a subterranean formation, comprising:
adding a scavenger compound to an analytical reagent to form a reagent solution;
collecting an amount of formation fluid into a formation tester,
wherein the formation tester comprises:
at least one fluids analyzer comprising at least one probe, at least one flow line, at least one reagent container, and at least one analyzer, wherein the fluids analyzer is configured such that the collected formation fluid is fed through the at least one flow line to the at least one analyzer;
mixing an amount of the collected formation fluid with an amount of the reagent solution to form a mixture; and
analyzing the mixture downhole,
wherein the adding a scavenger compound comprises adding a free radical scavenger compound having an adjustable scavenging capacity based on the analytical reagent to the analytical reagent.

2. The method of claim 1, further comprising:
storing the reagent solution in the at least one reagent container prior to transporting the formation tester downhole; and
transporting the formation tester downhole.

3. The method of claim 1, further comprising:
selecting the scavenger compound based on system and environment conditions.

4. The method of claim 1, wherein the free radical scavenger compound comprises at least one of an alcohol, a phenol, a thiol, an amine, a phosphine, a silane, a siloxane, or an alkyl halide.

5. The method of claim 1, wherein the free radical scavenger compound comprises at least one of butyl hydroxy toluene, butyl hydroxyanisole, tertiary butyl hydroquinone, mono-tert butyl-hydroquinone, ascorbic acid, isopropyl alcohol, or propyl gallate.

6. The method of claim 1, wherein the analytical reagent comprises at least one of a polymer-based solution, an organic dye containing solution, simple organic molecules dissolved in a solvent, polyelectrolytes dissolved in a solvent, or combinations thereof.

7. The method of claim 6, wherein the analytical reagent comprises at least one of an organic polymer, a water-soluble polymer, a polymer-nanoparticle mixture, and combinations thereof.

8. The method of claim 1, further comprising:
allowing a chemical reaction to occur subsequently to the mixing step, wherein the chemical reaction produces an endproduct; and
stabilizing the endproduct of the chemical reaction, wherein the scavenger stabilizes the endproduct.

9. The method of claim 1, wherein the analyzing comprises performing analysis on the mixture to determine at least one of optical absorbance, turbidity, fluorescence, conductivity, resistivity, magnetic resonance, or combinations thereof.

10. The method of claim 9, wherein the analyzing comprises performing reagent solution injection on the mixture, wherein the performing reagent solution injection spectral analysis includes injecting the reagent solution into the formation fluid within the flow line to create a mixture of formation fluid and reagent solution in the flow line.

11. The method of claim 10, further comprising:
establishing and storing baseline optical density values for at least one wavelength prior to injection of the reagent solution.

12. A composition for preventing and reducing the severity of chemical degradation caused by free radical attacks to chemical compounds and fluids used in downhole tools and oilfield operations, comprising:
- an analytical reagent;
- a scavenger compound,
- wherein the scavenger compound is a free radical scavenger and has an adjustable scavenging capacity based on the analytical reagent.

13. The composition of claim 12, wherein the free radical scavenger comprises at least one of an alcohol, a phenol, a thiol, an amine, a phosphine, a silane, a siloxane, and an alkyl halide, or combinations thereof.

14. The composition of claim 12, wherein the free radical scavenger comprises at least one of hydroxyl, hydroquinone derivatives and hindered amine functional groups or mixtures thereof.

15. The composition of claim 14, wherein the free radical scavenger compound comprises at least one of butyl hydroxy toluene, butyl hydroxyanisole, tertiary butyl hydroquinone, mono-tert butyl-hydroquinone, ascorbic acid, isopropyl alcohol, propyl gallate, or combinations thereof.

16. The composition of claim 12, wherein the analytical reagent comprises at least one of a polymer-based solution, an organic dye containing solution, simple organic molecules dissolved in a solvent, polyelectrolytes dissolved in a solvent, or combinations thereof.

17. The composition of claim 16, wherein the polymer-based solution comprises at least one of an organic polymer, a water-soluble polymer, a polymer-nanoparticle mixture, or combinations thereof.

* * * * *